United States Patent [19]

Newman

[11] Patent Number: 5,536,234
[45] Date of Patent: Jul. 16, 1996

[54] OPTICAL SURGICAL DEVICE WITH SCRAPING TOOL

[75] Inventor: Allen Newman, Tarzana, Calif.

[73] Assignee: Vista Medical Technologies, Inc., Carlsbad, Calif.

[21] Appl. No.: 400,919

[22] Filed: Mar. 8, 1995

Related U.S. Application Data

[63] Continuation of Ser. No. 108,980, Aug. 18, 1993, abandoned.

[51] Int. Cl.⁶ ............................ A61B 1/307; A61B 1/012
[52] U.S. Cl. .......................... 600/104; 600/135; 600/129; 600/156; 604/55; 604/280; 128/758
[58] Field of Search ........................ 600/104, 105, 600/116, 127, 129, 135, 156; 604/96, 280, 20, 46, 47, 55; 606/159, 160, 161; 128/757, 758, 750

[56] References Cited

U.S. PATENT DOCUMENTS

| | | | |
|---|---|---|---|
| 1,680,490 | 8/1928 | Wappler | 128/7 |
| 2,691,370 | 10/1954 | Wallace | 606/159 X |
| 2,990,830 | 7/1961 | Hett | 128/4 |
| 3,636,940 | 1/1972 | Graviee | 128/750 |
| 3,720,203 | 3/1973 | Brown | 128/4 |
| 4,243,049 | 1/1981 | Goodale et al. | 128/757 |
| 4,685,449 | 8/1987 | Bonnet | 128/4 |
| 4,690,175 | 9/1987 | Ouchi et al. | 128/4 X |
| 4,765,314 | 8/1988 | Kolditz et al. | 128/4 |
| 4,779,611 | 10/1988 | Grooter et al. | 128/4 |
| 4,836,187 | 6/1989 | Iwakoshi et al. | 128/4 |
| 4,841,952 | 6/1989 | Sato et al. | 128/6 |
| 4,860,731 | 8/1989 | Matsuura | 128/6 |
| 4,889,106 | 12/1989 | Watanabe | 128/4 |
| 4,979,498 | 12/1990 | Oneda et al. | 128/6 |
| 4,998,527 | 3/1991 | Meyer | 128/6 |
| 5,030,227 | 7/1991 | Rosenbluth et al. | 604/96 X |
| 5,031,603 | 7/1991 | Gautier et al. | 128/4 |
| 5,127,393 | 7/1992 | McFarlin et al. | 128/4 |
| 5,152,277 | 10/1992 | Honda et al. | 128/4 |
| 5,156,590 | 10/1992 | Vilmar | 128/4 X |
| 5,213,093 | 5/1993 | Swindle | 128/6 |
| 5,230,621 | 7/1993 | Jacoby | 128/6 X |
| 5,285,795 | 2/1994 | Ryan et al. | 128/4 X |
| 5,328,365 | 7/1994 | Jacoby | 128/6 X |

Primary Examiner—Richard J. Apley
Assistant Examiner—John P. Leubecker
Attorney, Agent, or Firm—Fish & Richardson

[57] ABSTRACT

An optical surgical device includes a detachable, disposable semi-flexible sheath for insertion into a patient's body. The sheath is provided with plurality of channels. One of the channels receives an endoscope for optical examination of an operative site within the patient. The remaining channels may be used for suction, drainage or irrigation of the operative site. The distal end of the sheath defines a hook-like scraping tool for removing tissue from the patient in the field of view of the endoscope.

26 Claims, 3 Drawing Sheets

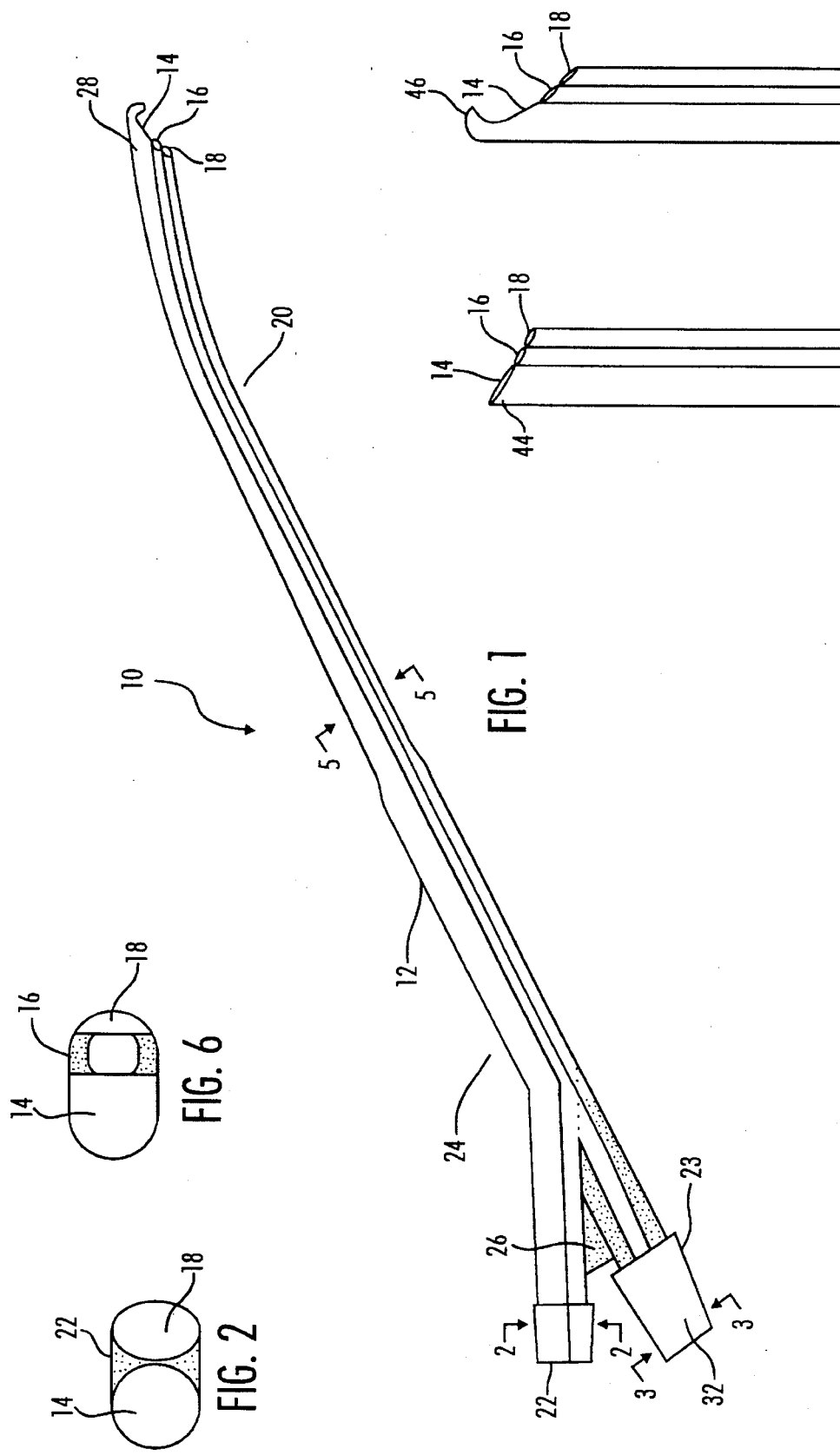

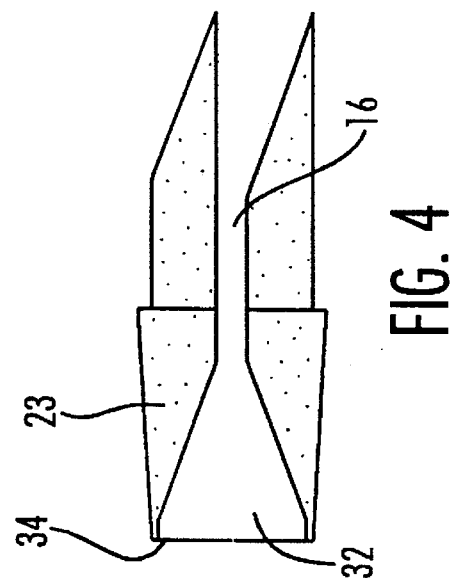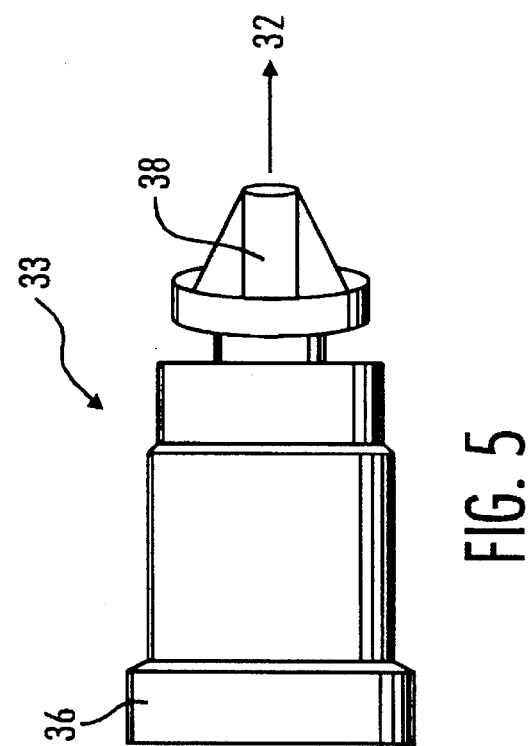

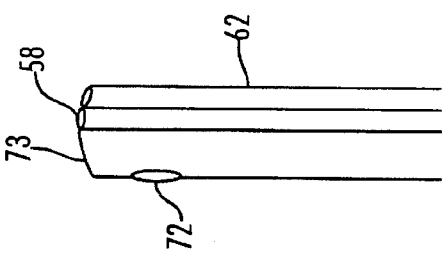
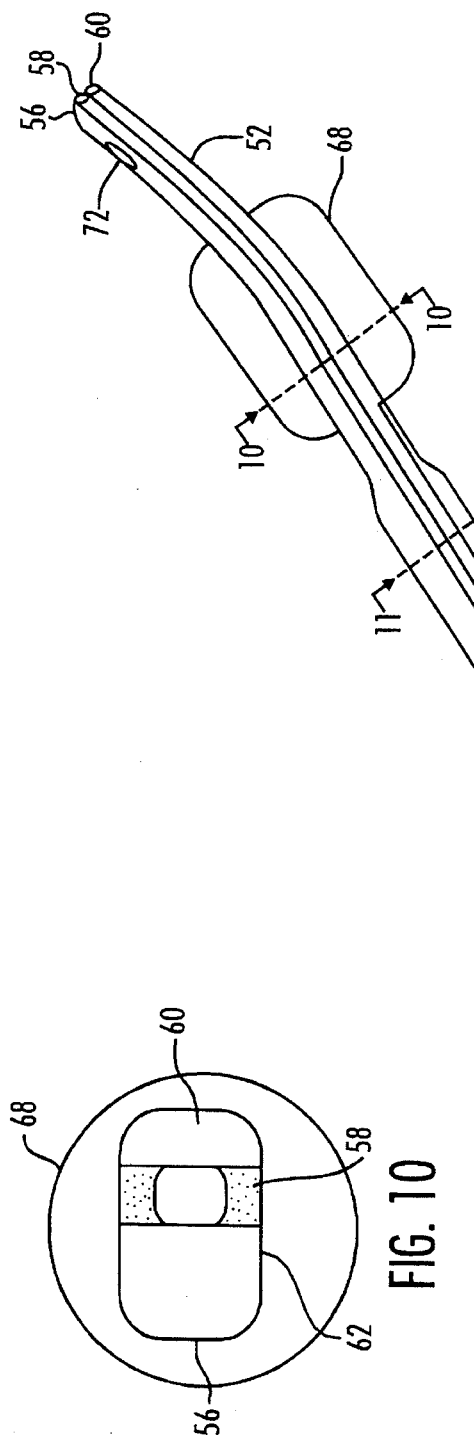
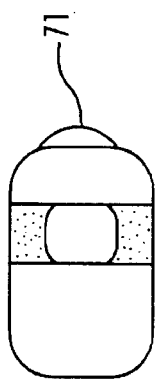
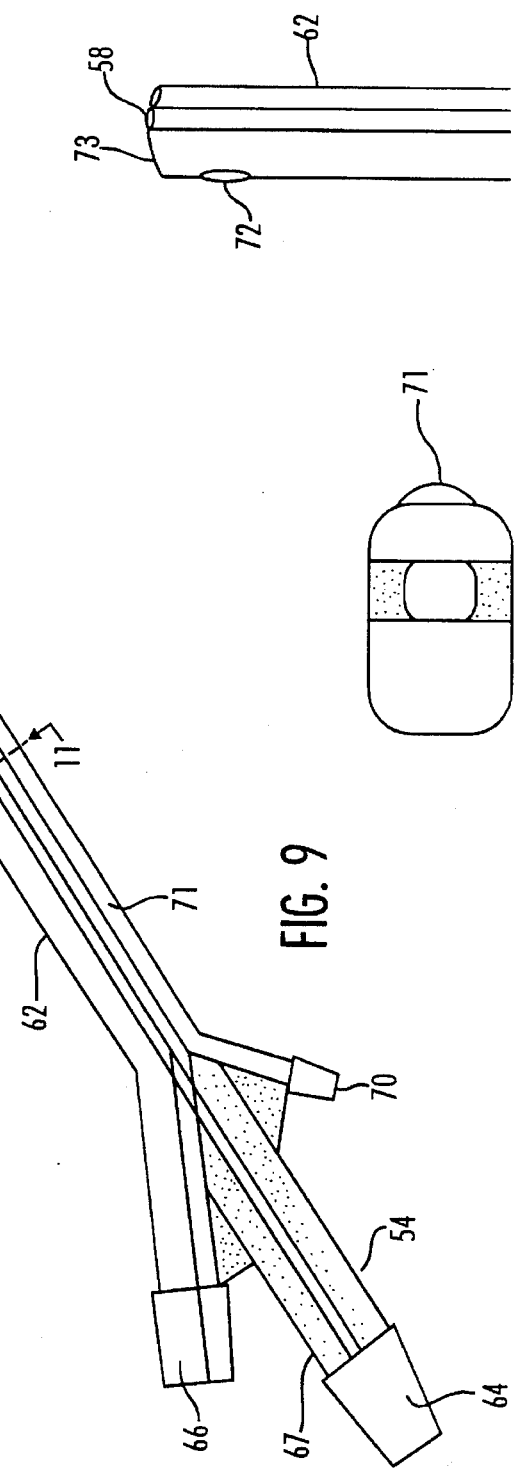

OPTICAL SURGICAL DEVICE WITH SCRAPING TOOL

This is a continuation of application Ser. No. 08/108,980 filed on Aug. 18, 1993, now abandoned.

BACKGROUND OF THE INVENTION

1. Field of the Invention

The present invention relates to optical medical devices for use in surgical procedures. In particular embodiments, the optical surgical device may be used to remove tissue, blood, or other liquid and particulate matter.

2. Description of Related Art

Certain gynecological procedures require a physician to examine, diagnose and often remove or extract tissue, blood, or other matter from an operative site within the patient. For example, in a one relatively common procedure, the physician must accurately locate uterine tissue to be removed, scraped, and/or aspirated. In other procedures, the physician may want to examine the patient's fallopian tubes or other internal areas to diagnose or biopsy other medical problems or difficulties, or simply to insure that the desired results have been achieved.

Different forms of endoscopes have been used to access and examine such operative sites within the patient's body. Typically, such endoscopes comprise bundles of long optic fibers which extend into the body cavity being examined. Some conventional endoscopes include multiple channels, or lumens, extending alongside or concentric with the optic fiber bundles. These channels may be used to introduce a flushing fluid into the operative site or to provide a conduit for other instruments to reach the desired area.

Conventional endoscopes, however, generally do not allow a continuous flow of irrigation fluid into the operative site to clean both the operative site as well as the endoscope, while simultaneously removing the fluid and other particulate matter from the area. Instead, in some conventional devices, a single lumen is designated for both suction and irrigation functions. As a result, suction and irrigation cannot occur simultaneously. The suction and irrigation functions must operate in an alternating fashion. In other devices in which separate channels are provided for inlet and outlet fluids, the corresponding openings typically operate so that a stream of fluid which is inlet through one port is later outlet through another port in an alternating fashion. Such an endoscopic device, however, still does not operate as a continuous flow system in which irrigation and suction can occur simultaneously and continuously.

Another drawback of some conventional endoscopic tools is that they are often uncomfortably large or wide in diameter. For example, many traditional endoscopes use glass rods and lenses to deliver light and display images. However, due to the materials and methods used, such relatively large devices have been known to cause significant discomfort during insertion and manipulation after being inserted. Often, due to the physical size limitations of the endoscope device, the physician may perform the surgery without visually examining the operative area.

One device which includes some of the drawbacks described above is shown in FIGS. 1–3 of U.S. Pat. No. 4,998,527 to Meyer (issued Mar. 12, 1991). Meyer discloses a complicated network of tubes combined in a metal sleeve. Each tube is designated for a specific function. For example, one of the tubes carries a resecting mechanism which breaks down large pieces of tissue into smaller pieces to be suctioned into another tube. As a consequence, however, the metal outer sleeve must be sufficiently large to retain the network of tubes, channels, etc.

Furthermore, conventional endoscopes are typically designed with rigid outer sleeves or sheaths made of a rigid plastic or metal material, such as that described above in the Meyer device. Such construction, however, is often difficult to manipulate within a patient's body, and generally requires extensive cleaning and sterilization after each use. Although some endoscopes incorporate both rigid and flexible materials for greater maneuverability during insertion and examination, such construction often requires substantial cleaning and sterilization to remove all contaminants trapped within the various crevices and openings of the different materials.

Moreover, it is particularly problematic to properly clean and sterilize tubes and conduits which form the lumens contained within conventional endoscopes. Because of the universal desire to maximize the patient's comfort during the examination, the lumens are typically designed to be as small as possible. However, such small openings tend to exacerbate the difficulty in properly cleaning and sterilizing the endoscope.

SUMMARY OF THE DISCLOSURE

Accordingly, it is an object of the present invention to provide an improved optical endoscopic device and method of making and using the same, obviating for practical purposes the above-mentioned limitations.

These and other objects and advantages are accomplished, according to an embodiment of the present invention, by an optical surgical device having an outer sheath constructed with multiple channels, or lumens, extending through the length of the sheath. The sheath, according to the illustrated embodiments, is disposable. Preferably, for each procedure, a new, presterilized sheath is used. This minimizes the risk of contamination and decreases the amount of time directed to the proper cleaning and sterilization of the sheath and multiple channel structure. Thus, the disposable feature significantly reduces the possibility of contamination and infection due to inadequate cleaning or sterilization of the sheath.

The sheath is preferably made of a semi-flexible plastic, vinyl or other material appropriate for the particular application. For example, the sheath may be formed of a rigid plastic with a curved end for use as a curette in, aspiration biopsies, or other procedure in which tissue or fluid is removed around the operative site. In addition, a flat-ended sheath may be used for other examination procedures such as for fallopian tube blockage or bowel endoscopy, for example.

In the illustrated embodiment of the sheath, three channels are shown disposed adjacent each other. An endoscope is provided in one of the channels of the sheath to enable the physician to optically examine the operative site within the patient. The endoscope is comprised of bundles of optic fibers which extend through the entire length of the corresponding channels in the sheath. The endoscope is first inserted into one of the channel openings at the proximal end of the sheath, and then fed through the channel until it reaches the end of the channel at the distal tip of the sheath. The endoscope can be quickly disengaged from the sheath by simply sliding it out of its designated channel.

The remaining channels may be occupied by suction and/or irrigation sources, or other medical devices. Preferably, the suction channel is the largest channel so that fluid or tissue scraped or removed from the operative site do not clog or block the pathway. A source of irrigation is supplied to flush the operative site, if necessary, as well as to clean the viewing area at the distal tip of the endoscope. The irrigation solution is simply supplied through the designated irrigation channel while the patient's bodily tissue and fluid, as well as the irrigation solution, are drained through the suction channel.

Thus, the above-described arrangement of the present invention allows the physician to visually examine, for example, a patient's uterus before, during and after an intrauterine procedure. The physician may irrigate or insufflate the operative site, accurately locate the target tissue, and then scrape and/or remove by suction the tissue. Because the disposable sheath is quickly removable and replaceable, a variety of different procedures may be used with a single endoscope. For example, other procedures which may also be performed using the illustrated embodiments of the present invention include aspiration biopsy, artificial insemination and fallopian tube examination. In addition, further embodiments of the present invention may be used as a pediatric cystoscope, amniocentesis scope, female urethroscope or as a male cystoscope.

BRIEF DESCRIPTION OF THE DRAWINGS

The detailed description will be made with reference to the accompanying drawings, wherein like numerals designate corresponding parts in the several figures.

FIG. 1 is a perspective view of an optical surgical device according to one embodiment of the present invention.

FIG. 2 is a cross-sectional view of a portion of the optical surgical device along the lines 2—2 shown in FIG. 1.

FIG. 3 is a cross-sectional view of a portion of the optical surgical device along the lines 3—3 shown in FIG. 1.

FIG. 4 is a side view of a portion of the optical surgical device of the embodiment in FIG. 1.

FIG. 5 is a perspective view of one aspect of the optical surgical device.

FIG. 6 is a cross sectional view of a portion of the optical surgical device along the lines 5—5 shown in FIG. 1.

FIG. 7 is a side view of a portion of one aspect of an optical surgical device.

FIG. 8 is a side view of a portion of another aspect of an optical surgical device.

FIG. 9 is a perspective view of an optical surgical device according to another embodiment of the present invention.

FIG. 10 is a cross-sectional view of a portion of the optical surgical device along the lines 10—10 shown in FIG. 9.

FIG. 11 is a cross-sectional view of a portion of the optical surgical device along the lines 11—11 shown in FIG. 9.

FIG. 12 is a side view of a portion of the optical surgical device of the embodiment shown in FIG. 9.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of embodiments of the invention. The scope of the invention is best defined by the appended claims.

FIG. 1 is a perspective view of an optical surgical device 10 according to an embodiment of the present invention. As discussed in more detail below, embodiments of the present invention are suitable for use in a variety of intrauterine or other internal examination procedures, such as, aspiration biopsy, artificial insemination techniques, amniocentesis, chorionic villa sampling, and urethra, urinary bladder and bowel endoscopy, for example. Embodiments of the present invention provide significant advantages in that the physician may more clearly examine the body cavity or operative area during the intrauterine or internal surgical procedure with minimal obstruction. In addition, other embodiments of the present invention allow for video documentation of the procedure if desired.

Thus, the physician may accurately locate the tissue to be removed, irrigate or insufflate the operative site, and scrape and/or use suction to remove the desired tissue, while concurrently viewing each step of the procedure. Consequently, the occurrence of inadvertent accidents such as perforation of the operative site or body cavity, e.g., the patient's uterus, is significantly reduced.

While various embodiments of the present invention may also be suitable for other surgical and diagnostic procedures, as described in more detail below, the described embodiments are preferably directed for use within any areas of a patient's body for which visual examination is particularly helpful. For example, during a biopsy procedure of tissue or fluid within a patient's urethra or bladder, optical diagnosis and examination of the surgical procedure may be especially useful. It will be recognized that further embodiments of the present invention may be suitable for various other biopsy procedures, such as (but not limited to) biopsies of the breast, lung, kidney, and almost any other internal organ or cavity in which optical probing capabilities are necessary to reach and ultimately examine the desired operative site.

As illustrated in FIG. 1, the optical surgical device 10 comprises, generally, an elongated sheath 12 containing multiple channels 14, 16, and 18. Each channel is designated for a specific function. For example, channel 14 may be designated for suction or drainage purposes. Preferably, the center channel 16 is designated for insertion of an endoscope (not shown). The endoscope may be inserted in the channel 16 at the proximal end 24 of the sheath 12, and pushed through to the distal end 20 of the sheath 12. The endoscope extends through the length of the sheath 12. The endoscope is preferably formed of a bundle of optical fibers which carry images from the distal end of the device to the proximal end. In addition, light delivery fibers may be provided for illuminating the examined area. Depending upon the configuration of the endoscope, a light source may be coupled to the endoscope fibers to illuminate the operative site.

The third channel 18 is provided as an irrigation line through which an irrigating or flushing fluid may flow to irrigate the operative site during the surgical procedure, while simultaneously cleaning the endoscope. In other embodiments, the irrigation channel 18 may be used, for example, as a gas inflow channel through which a gas, such as carbon dioxide ($CO_2$), may be directed to insufflate the operative site.

It will be recognized that the suction and irrigation functions may be performed using the designated channels in the sheath 12 through separate tubing which may be connected to the channels provided in the sheath 12. For example, individual suction and irrigation tubes, or lines, may be attached to the external sources of the suction and irrigation. Thus, the preformed, predefined channels themselves may comprise the pathways for suction and irrigation.

As illustrated in FIG. 1, the proximal end 24 (on the left side of the figure) of the optical surgical device 10 is provided with two ports 22 and 23. As shown in FIG. 2, the suction/irrigation port 22 includes the proximal openings for the suction and irrigation channels 14 and 18, respectively. In FIG. 3, the cross-section of the proximal endoscope port 23 shows the endoscope channel 16 and viewing area at approximately the center of the port 23. Preferably, the suction/irrigation port 22 is offset from the proximal endoscope port 23 for reasons discussed below.

As shown in FIGS. 1 and 4, an eyepiece port 32 is coupled to the open end of the proximal endoscope port 23. Preferably, the eyepiece port 32 extends along the same line as the sheath 12 and endoscope channel 16. The in-line construction of the eyepiece port 32 facilitates easier access to the viewing angle as the sheath 12 is rotated or manipulated within the operative site. Otherwise, if the eyepiece port is offset from the body of the sheath and endoscope, as in some conventional endoscopes, the physician must physically adjust his or her viewing position to accommodate the changing position of the rotating eyepiece port. Instead, in preferred embodiments of the present invention, the physician does not have to sacrifice balance and control of the optical device while adjusting the position of the device during the examination procedure.

The eyepiece port 32 is attached over the endoscope port 23 at the proximal end 24 of the sheath 12. The funnel-shaped eyepiece port 32 receives a conical eyepiece 33 (FIG. 5). Preferably, a metal or rigid covering surrounds the optical fibers of the endoscope for coupling to the distal end of the eyepiece 33. Various eyepieces 33 may be used for different examination procedures. For example, depending upon the desired degree of optical examination, the eyepiece may require magnifying or focusing capabilities. A preferred eyepiece embodiment, as illustrated in FIG. 5, includes a focusing ring 36 located at the proximal end of the eyepiece 33 for manual adjustment by the user. It will be recognized, however, that various other manual or automatic focusing and magnifying techniques may be implemented to enable a clear, focused view of the operative site through the eyepiece and endoscope assembly.

The distal end of the eyepiece 33 is provided with a conical-shaped locking mechanism 38 for attachment to the eyepiece port 32, shown in FIG. 4. The locking mechanism 38 is inserted into the funnel shaped opening of the eyepiece port 32 for a secure fit. Preferably, a screw-on type locking mechanism is used to screw the eyepiece 33 to the eyepiece port 32. However, other friction-fit devices or methods may also be used to ensure a tight seal between the eyepiece and the sheath. In addition, a gasket 34 may be used to further prevent leakage of irrigating solution and other fluid, or to prevent the insufflating gas from escaping, around the periphery of the eyepiece port connection. Alternatively, port 32 can be integrally formed on the proximal end 24 of the sheath 12.

A preferred eyepiece has been developed by Ideation Engineering in which glass lenses and prisms are used to magnify and focus images seen through the endoscope. A focusing ring is provided on the eyepiece. The conical-shaped eyepiece includes a cone-shaped locking mechanism which can be twist-fit into the eyepiece port. The eyepiece may be connected to a medical video camera or may be used for direct viewing.

As described above, the suction/irrigation port 22 is preferably offset from the proximal endoscope port 23 to prevent obstruction of or interference with the viewing area around the endoscope eyepiece, as well as to separate the sources of fluid or gas from the eyepiece. Depending upon the rigidity of the material which forms the sheath 12 and the ports 22 and 23, an angle support brace 26 may be provided in the angular separation between the suction/irrigation port 22 and the proximal endoscope port 23. For example, if the sheath and the respective channels and ports are made of a flexible material, the angle support brace 26 may be used to keep the tubing, cables, etc. of the suction and irrigation supply lines from draping over the endoscope eyepiece. Thus, the support brace 26 functions to maintain and brace the separation between the two ports to avoid obstruction of the endoscope viewing area by the suction/irrigation supply lines.

FIG. 2 shows the suction/irrigation port 22 divided into two channel openings 14 and 18. The diameters of the suction and irrigation channels may vary depending upon the desired use for the optical surgical instrument. For example, the cross-section of the suction (or drainage) channel 14 may be larger than that of the irrigation channel 18. Thus, if the tissue to be removed around the operative site is primarily comprised of the endometrial lining of the uterus, it may be desirable to have a large suction channel 14 relative to the irrigation channel 18 so that the tissue can be scraped and removed from the operative area without clogging the channel. Simultaneously, the operative site may be irrigated with a thin, continuous stream of water or other irrigating solution.

For other procedures such as, for example, aspiration biopsy or fallopian tube insemanation, the suction channel 14 may be small relative to the irrigation channel 18 to limit or control the amount of tissue and/or fluid injected into or removed from the operative site. For example, in an insemination procedure, it may be desirable to employ a sheath having a large irrigation channel for use as a fluid injection channel. A "suction" function then may be completely unnecessary.

As shown in FIG. 2, the proximal openings of the suction and irrigation channels 14 and 18, respectively, are circular or oval in shape. It will be recognized that the particular configuration, shape, and size of each of the channels within the sheath 12 may vary according to the particular application. For example, the shapes of the suction channel 14 and the irrigation channel 18 will preferably be circular if standard-gauge tubing is used, rather than using the channels as direct conduits between the suction/irrigation port 22 and the distal tip 28 of the sheath. The sheath, as well as the channels contained therein, may thus have a variety of shapes and lengths for use in different surgical procedures.

In any internal examination procedure, however, the sheath preferably contains a minimum number of channels necessary to perform the medical procedure, yet ensure patient comfort during insertion and manipulation of the surgical device. Thus, to meet the needs for patient comfort and controllability of the device during the surgical procedure, the sheath structure 12 of the described embodiments is tapered, as illustrated in FIG. 1. The diameter of the sheath 12 is larger at the proximal end 24 as compared to the distal end 20 of the sheath 12. Because the distal half 20 of the sheath 12 is inserted into the patient during the operative procedure, the slim configuration of the distal end 20 of the sheath 12 minimizes patient discomfort during insertion and enhances maneuverability during the examination procedure. Similarly, the wider proximal end of the sheath 12 provides for easy handling and control of the sheath 12 by the physician.

In another aspect of the illustrated embodiment, the sheath material is preferably semi-flexible to allow the physician to maneuver the sheath into the desired location and position, yet sufficiently rigid for proper control of the endoscope during the examination. Thus, the materials used to form the sheath 12 may vary depending upon the procedure to be performed. Furthermore, the walls of the proximal half 24 of the sheath may be constructed to be thicker, and therefore more rigid, than those of the distal end 20 of the sheath. In such a configuration, although the diameters of the channels within the sheath 12 may be uniform through the entire length of the sheath, the external structure of the sheath may nevertheless be tapered to enhance flexibility and manipulability of the sheath during an examination.

FIG. 6 shows a cross-section of the distal half 20 of the sheath 12. In the illustrated embodiment, the suction, endoscope, and irrigation channels are arranged in a side-by-side fashion. The suction channel 14 is shown larger than the endoscope and irrigation channels 16 and 18, respectively. As described above, the suction channel 14 is preferably sufficiently large to facilitate the removal of blood and other substances around the operative site. The center channel 16 accommodates the endoscope (not shown). Preferably, the width of the endoscope channel 16 is approximately 1 mm. The remaining lumen 18 provides a path for irrigation or insufflation of the operative site. This channel is also preferably approximately 1 mm in size.

The overall diameter of the distal portion 20 of the sheath preferably ranges between 3 mm and 7 mm. It will be recognized that the width of the distal portion 20 of the sheath 12 is significantly smaller than many conventional optical surgical tools to provide increased patient comfort, and adjustability and control of the surgical device during the operative procedure. The selected size, however, will vary depending on the number of channels necessary for the particular surgical procedure.

In yet another aspect of the illustrated embodiments of the present invention, the shape of the distal tip 28 of the sheath 12 may vary depending upon the particular application of the optical surgical device 10. The particular tip structure may be selected to allow the physician to directly view and precisely locate the desired operative site, and then scrape and/or suction the target tissue or fluid. Examples of curved and blunt distal tips are shown in FIGS. 1, 7 and 8. A curved tip 46 (FIGS. 1 and 7), for example, provides both physical and visual access to nearly any area of an operative site as the sheath 12 is rotated or manipulated manually by the physician. The curved tip 46 may be useful in procedures such as aspiration biopsies. The hook-like configuration facilitates the dislodging of the desired tissue from the operative site (e.g., the endometrial lining of the uterine wall), and directs the dislodged tissue into the suction channel 14. Preferably, the curved tip 46 is positioned sufficiently beyond the distal opening of the endoscope channel 16 to avoid obstruction of the endoscope.

In another preferred embodiment of the invention, the sheath 12 may be provided with a blunt tip 44 (FIG. 8) which may be useful in intrauterine procedures. The blunt tip 44 allows the physician to clearly view the desired tissue, place the tip adjacent the tissue, and remove the tissue by scraping or suction. A sheath having a blunt tip 44 may also be used in tubal insemination procedures in which the distal tip of the optical surgical device is inserted into a patient's fallopian tubes. The blunt configuration of the tip provides an unobstructed view into the openings of the fallopian tubes. In operation, the physician simply places the blunt tip near the openings of the fallopian tubes so that the semen held in one of the channels in the sheath can be accurately injected into the tubal openings.

As illustrated in FIGS. 1, 7 and 8, the endoscope channel 16 is disposed between the suction and irrigation channels 14 and 18, respectively. Such a configuration provides for continuous cleansing of the tip of the endoscope during the surgical procedure. The continuous flow of irrigating fluid provides an unobstructed view of the operative site through the endoscope. In addition, the irrigating fluid may be supplied or delivered only on demand. For example, if a continuous flow of irrigating fluid is unnecessary, if the view through the endoscope becomes clouded by blood or other tissue, the tip can instantly be cleaned by applying suction and irrigation simultaneously. Thus, as the irrigating fluid flows into the operative site, across the tip of the endoscope, the fluid and any tissue may be quickly flushed out and extracted through the suction channel 14.

In another preferred embodiment of the present invention, the optical surgical device may be used for examining a patient's urethra and bladder. An embodiment of an optical urethroscope 50 is illustrated in FIG. 9. When used to examine female patients, the distal end 52 of the urethroscope 50 is inserted into the patient's urethra, similar to the operation of the optical surgical device 10. Thus, preferably, the distal end 52 of the urethroscope 50 is slimmer, i.e., has a smaller diameter, than the proximal end 54.

The urethroscope 50 may be provided with multiple channels, or lumens 56, 58 and 60 formed within an outer sheath 62. Preferably, an endoscope (not shown) is inserted into the center channel 58 of the sheath 62. A drainage channel 56 is designated for outflow of fluids from the urethra, while an irrigation channel 60 is provided for inflow of irrigating fluid.

The urethroscope 50 may also include an eyepiece coupled to an eyepiece port 64 at the proximal end 54 of the sheath 62, as shown in FIG. 9. A gasket may be inserted between the eyepiece port 64, at proximal end of the endoscope channel 58 of the sheath 62, and the eyepiece to prevent leakage of urine or other fluid around the eyepiece during use. FIG. 9 shows the eyepiece port 64 extending generally in-line with the elongated body of the sheath 62. As described earlier, such a configuration provides direct viewing capability of the operative site without requiring the physician or video apparatus to be shifted or moved whenever the sheath and eyepiece arrangement are rotated or adjusted.

Like the embodiment of the optical surgical device 10 illustrated in FIG. 1, the drainage channel 56 and irrigation channel 60 form the drainage/irrigation port 66 which is offset from the proximal endoscope port 54. The size and structure of the drainage and irrigation channels 56 and 60 may be substantially configured to fit standard drainage and irrigation connectors and tubing.

In another aspect of the urethroscope embodiment of the present invention, the urethroscope may be equipped with an inflation medium, such as a balloon, to dilate the urethra, if necessary. Rather than using the conventional method of inserting graduated sizes of metal rods to dilate the urethra, the urethroscope may be used for both examination as well as dilation. As shown in FIGS. 9–11, a balloon 68 may be provided around part of the distal end 52 of the sheath 62. The balloon preferably is formed of a plastic or rubber material wrapped around the outer circumference of the distal section 52 of the sheath to be inserted into the patient.

The balloon 68 is coupled to a balloon inflation channel 71. The balloon inflation channel 71 extends longitudinally adjacent the irrigation channel 60, as indicated in FIG. 11. An external source of an inflating medium (not shown) may be coupled to the balloon inflation channel 71 at the balloon inflation port 70 shown in FIG. 9. In the illustrated embodiment, the balloon inflation port 70 is angled away from the balloon inflation channel 71, and therefore the body of the sheath 62, to facilitate easy hook-up to the inflation medium and minimize obstruction of the viewing area. Preferably, the balloon inflation port 70 comprises a luer lock system in which water, air or other inflating gas that has been injected into the balloon through the balloon inflation port 70 cannot escape. The luer lock essentially acts as a one-way gas inlet.

Accordingly, during an examination procedure of the urethra, for example, after the physician has inserted the urethroscope 50 into the patient's urethra, the physician may quickly, yet controllably dilate the urethra by inflating the balloon 68. As the balloon expands, the urethra is slowly forced to expand, or dilate. FIG. 10 illustrates a cross-section of the inflated balloon 68 surrounding the sheath 62. Preferably, the balloon 68 extends from outside of the patient to beyond the length of the urethra so that the entire length of the patient's urethra may be dilated with minimal trauma and discomfort.

The size and construction of the described embodiment of the urethroscope may be varied to accommodate different patients and procedures while minimizing discomfort. For example, the distal half 52 of the sheath 50 (which will be inserted into a patient) preferably is curved, as shown in FIG. 9. The slight curvature provides sufficient flexibility and access both physically and visually to the various areas of the operative site being examined. In addition, the distal tip 73 of the illustrated embodiment of the urethroscope may be rounded (FIG. 12) to facilitate more comfortable insertion. Preferably, the endoscope is inserted into the central channel 58 of the sheath 62 such that the endoscope viewing area protrudes from the rounded tip 73 of the sheath. As a result, the endoscope field of view is increased.

As illustrated in FIGS. 9 and 12, the drainage opening 72 at the distal end of the drainage channel 56 may be skewed off to the side of the tip 73 of the sheath 62. Since drainage is a passive function, in contrast to active suction, the physician typically does not need to directly viewed the drainage of fluid through the drainage opening 72 during the examination procedure. Thus, the drainage opening 72 is preferably located to the side of the sheath tip to minimize interference with the optical examination, as shown in FIGS. 9 and 12. In an alternate embodiment, drainage channel 56 may be eliminated.

Like the optical surgical device, the urethroscope sheath 62 is preferably made of a semi-flexible material to provide for comfortable insertion and manipulation with the patient. However, as discussed above, the sheath material must be sufficiently rigid at the proximal end of the sheath to enable the physician to properly maneuver the distal end of the sheath into the desired location. Accordingly, the diameter of the sheath 62 is larger toward the proximal end 54 for increased strength and manipulability. The sheath is tapered toward its distal end 52 to minimize patient discomfort.

With regard to the described embodiments of the optical surgical device and the urethroscope device, the sheath 12 and 62 is disposable. Preferably, each sheath will be designated for single patient use only. After each examination or surgical procedure in which the sheath has been inserted into the patient, the suction (or drainage)/irrigation port may be simply disconnected from the suction and irrigation sources, and the eyepiece and endoscope may be easily removed from (e.g., slipped out of) the respective endoscope channel. Consequently, the remaining empty sheath can be immediately disposed of without further cleaning or sterilization. Only the endoscope and the eyepiece may require cleaning and sterilization for future use. Thus, because of the disposable feature of the outer sheath, the time and energy which would otherwise be required to properly clean and sterilize the sheath are significantly reduced.

In addition, because the sheath is presterilized before each single use, the physician simply needs to remove the already-sterilized sheath from its packaging, attach it to the necessary suction/drainage and irrigation sources, insert the endoscope and attach the eyepiece. The surgical device is then ready for immediate use. Such construction significantly decreases the complexity and margin for error during examinations and other operative procedures.

In the illustrated embodiments, the eyepiece coupled to the proximal end of the sheath and endoscope channel is arranged in-line with the sheath for direct viewing capability. However, it will be recognized that depending upon the particular application or position of the patient during the operative procedure, the eyepiece may be angled away from the body of the sheath. Similarly, the suction (or drainage)/ irrigation port may be configured in a variety of other ways not shown in the illustrated embodiments to accommodate different configurations and positions as necessitated by the examination procedure.

In addition, further embodiments may employ different numbers of channels as necessary for attachment to a variety of devices and/or sources necessary for different operative procedures. For example, a channel may be designated for the introduction of other instruments, such as a biopsy instrument for use in the patient's urinary bladder. Also, it will be recognized that other optical devices may be used to observe the operative procedure.

The presently disclosed embodiments are to be considered in all respects as illustrative and not restrictive. The scope of the invention being indicated by the appended claims, rather than the foregoing description, and all changes which come within the meaning and range of equivalency are, therefore, intended to be embraced therein.

We claim:

1. An optical surgical apparatus operable with an optical viewing device for examination of the genitourinary tract of a patient, the apparatus comprising:

a disposable tube-shaped member having:

an open proximal end and an open distal end, the tube-shaped member being semi-flexible and dimensioned for comfortable insertion into the genitourinary tract of a patient, the overall diameter of the distal end being in the range of about 3 mm to about 7 mm, and the distal half of the tube-shaped member being slightly curved for ease of insertion and viewing access within a patient;

at least two channels integrally formed within the tube-shaped member and extending between the open proximal end and the open distal end, including an endoscope channel for removably receiving the optical viewing device, and an irrigation channel for directing fluid to the operative site and to clean the distal end of the optical viewing device; and a port at the open proximal end of the tube-shaped member communicating with the endoscope channel, for removably receiving the optical viewing device;

wherein the distal end of the tube-shaped member defines a scraping tool for soft tissue, and the endoscope channel is positioned at the distal end of the member for causing the optical viewing device, when received in the endoscope channel, to provide a view of a soft-tissue surface being scraped by the scraping tool.

2. The optical surgical apparatus of claim 1, wherein the port at the proximal end of the endoscope channel is co-axial with the tube-shaped member.

3. The optical surgical apparatus of claim 1, wherein the diameter of the distal end of the channel which receives the optical viewing device is approximately 1 mm.

4. The optical surgical apparatus of claim 1, wherein the tube-shaped member tapers from the proximal end to the distal end.

5. An optical surgical system for examination of the genitourinary tract of a patient, comprising:

a disposable tube-shaped member having a plurality of integral channels extending therethrough, the tube-shaped member having an open proximal end and an open distal end, the tube-shaped member being semi-flexible and dimensioned for comfortable insertion into the genitourinary tract of a patient, the overall diameter of the distal end being in the range of about 3 mm to about 7 mm, and the distal half of the tube-shaped member being slightly curved for ease of insertion and viewing access within a patient;

an optical viewing device removably received by one of the channels in the tube-shaped member at the open proximal end of the tube-shaped member and having a field of view at the distal end of the tube-shaped member;

an irrigation supply in flow communication with another one of the channels in the tube-shaped member, such channel being positioned for directing irrigation fluid to the operative site and to clean the distal end of the optical viewing device; and scraping means for scraping soft tissue in the field of view of the optical viewing device; and means for removing scraped tissue and fluid from the patient, the means for removing tissue and fluid being coupled to another channel in the tube-shaped member defining a drainage channel, wherein the tissue and fluid enter the drainage channel at the open distal end of the tube-shaped member and exit the drainage channel at the open proximal end of the tube-shaped member.

6. The optical surgical system of claim 5, wherein the the proximal end of the channel receiving the optical viewing device is co-axial with the tube-shaped member.

7. The optical surgical system of claim 5, wherein the diameter of the distal end of the channel which receives the optical viewing device is approximately 1 mm.

8. The optical surgical system of claim 5, wherein the drainage channel has the largest diameter of the plurality of channels in the tube-shaped member.

9. An optical surgical system for examination of tissue and fluid in the genitourinary tract of a patient, comprising:

a disposable sheath having a plurality of integral channels extending therethrough, the plurality of integral channels defining at least first, second and third channels, the sheath having a proximal end and a distal end, the distal end of the sheath for inserting into the patient, the sheath being semi-flexible and dimensioned for comfortable insertion into the genitourinary tract of a patient, the overall diameter of the distal end of the sheath being in the range of about 3 mm to about 7 mm, and the distal half of the sheath being slightly curved for ease of insertion and viewing access within a patient;

an optical viewing device removably received by the first channel in the sheath at the proximal end of the sheath, wherein the optical viewing device extends from the proximal end to the distal end of the sheath and has a field of view at the distal end of the sheath;

an irrigating source in flow communication with the second channel in the sheath, the irrigating source including an irrigating solution to irrigate the patient and clean the distal end of the optical viewing device; and the distal end of the sheath having a scraping tool for removing tissue from the patient in the field of view of the optical viewing device, the scraping tool being proximate to the third channel in the sheath, wherein scraped tissue and fluid enter the third channel at the distal end of the sheath and exit the third channel at the proximal end of the sheath.

10. The optical surgical system of claim 9, wherein the first channel containing the optical viewing device is disposed between the second and third channels.

11. The optical surgical system of claim 9, wherein the optical viewing device comprises a bundle of optic fibers.

12. The optical surgical system of claim 9, further comprising an eyepiece coupled to the optical viewing device at the proximal end of the sheath, wherein the eyepiece extends along the same line as the sheath.

13. The optical surgical system of claim 12, further comprising a gasket coupled to the eyepiece for preventing leakage of tissue, fluid, and irrigating solution into the eyepiece.

14. The optical surgical system of claim 12, wherein the eyepiece includes a locking member for attaching to the optical viewing device.

15. The optical surgical system of claim 12, wherein the eyepiece includes a focusing mechanism for magnifying and focusing an image viewed through the optical viewing device.

16. The optical surgical system of claim 12, further comprising a removal/irrigation port for coupling to external sources of removal and irrigation, the removal/irrigation port being disposed at an angle from the eyepiece coupled to the optical viewing device at the proximal end of the sheath.

17. The optical surgical system of claim 16, further comprising a brace for supporting the angle between the removal/irrigation port and the eyepiece.

18. An endoscope assembly for optical examination of tissue and fluid around an operative site within the genitourinary tract of a patient, comprising:

a disposable sheath having a plurality of integral channels extending therethrough, and having a proximal end and a distal end, the distal end of the sheath having a tip for inserting into the operative site and defining a scraping tool for scraping soft tissue at the operative site, the sheath being semi-flexible and dimensioned for comfortable insertion into the genitourinary tract of a patient, the overall diameter of the distal end of the sheath being in the range of about 3 mm to about 7 mm, and the distal half of the sheath being slightly curved for ease of insertion and viewing access within a patient;

a fiber-optic viewing device removably received by one of the channels in the sheath defining a viewing channel, wherein the fiber-optic viewing device extends from the proximal end of the sheath to the tip of the distal end of the sheath and has a field of view at the distal end of the sheath, which field of view overlaps the operative site when the scraping tool is scraping tissue at the operative site;

irrigation means for irrigating the operative site with an irrigating solution, the irrigation means coupled to another one of the channels in the sheath defining an irrigation channel, wherein the irrigating solution simultaneously cleans the fiber-optic viewing device; and drainage means for removing tissue and fluid from the operative site, the drainage means coupled to another one of the channels in the sheath defining a drainage channel, wherein the tissue and fluid from the operative site enter the drainage channel at the distal end of the sheath and exit the drainage channel at the proximal end of the sheath.

19. The endoscope assembly of claim 18, wherein the viewing channel is disposed between the irrigation and drainage channels.

20. The endoscope assembly of claim 18, wherein the drainage channel has the largest diameter of the plurality of channels in the sheath.

21. The endoscope assembly of claim 18, further comprising:

an eyepiece coupled to the fiber-optic viewing device at the proximal end of the sheath, wherein the eyepiece extends along the same line as the sheath, and a drainage/irrigation port for coupling to external sources of removal and irrigation, wherein the irrigation channel and the drainage channel are separated from the viewing channel such that the drainage/irrigation port is skewed at an angle away from the eyepiece at the proximal end of the sheath to facilitate easier manipulation and rotation of the sheath during the examination.

22. The endoscope assembly of claim 21, wherein the eyepiece further includes:

a locking member for attaching the eyepiece to the fiber-optic viewing device, and a focusing mechanism for magnifying and focusing an image viewed through the fiber-optic viewing device.

23. A method of making an optical surgical apparatus for optically examining tissue and fluid around an operative site within the genitourinary tract of a patient, comprising the steps of:

providing a disposable sheath having a plurality of channels extending therethrough, an open proximal end and an open distal end defining a scraping tool, the distal end of the sheath for inserting to the operative site, wherein a first one of the channels defines a viewing channel, a second one of the channels defines an irrigation channel, and a third one of the channels defines a drainage channel, the sheath being semi-flexible and dimensioned for comfortable insertion into the genitourinary tract of a patient, the overall diameter of the distal end of the sheath being in the range of about 3 mm to about 7 mm, and the distal half of the sheath being slightly curved for ease of insertion and viewing access within a patient;

inserting an endoscope into the viewing channel in the sheath, the endoscope extending from the proximal end of the sheath to the distal end of the sheath, the proximal end of the sheath and endoscope defining a viewing port, the endoscope having, at the distal end of the sheath, a field of view in the vicinity of the scraping tool;

attaching an eyepiece to the viewing port; and separating a drainage/irrigation port from the eyepiece, the drainage/irrigation port for coupling to external sources of drainage and irrigation.

24. A method of using an optical surgical apparatus for optically examining tissue and fluid at an operative site within the genitourinary tract of a patient, comprising the steps of:

inserting an endoscope into one of a plurality of channels extending through a disposable sheath, the sheath having a proximal end and a distal end, the distal end defining a scraping tool for scraping tissue at the operative site the endoscope extending from the proximal end of the sheath to the distal end of the sheath, the proximal end of the sheath and endoscope defining a viewing port, further wherein the plurality of channels define an irrigation channel and a drainage channel, the sheath being semi-flexible and dimensioned for comfortable insertion into the genitourinary tract of a patient, the overall diameter of the distal end of the sheath being in the range of about 3 mm to about 7 mm, and the distal half of the sheath being slightly curved for ease of insertion and viewing access within a patient;

coupling sources of drainage and irrigation to the drainage and irrigation channels;

inserting the distal end of the sheath to the operative site;

scraping soft tissue at the operative site with the scraping tool while viewing the operative site through an eyepiece coupled to the viewing port; and discarding the sheath following the above steps.

25. The method of claim 24, further comprising the step of irrigating the operative site with an irrigating solution through the irrigation channel.

26. The method of claim 24, further comprising the step of removing tissue, fluid and irrigating solution from the operative site through the drainage channel.

* * * * *